United States Patent
Leon et al.

(10) Patent No.: US 6,482,931 B2
(45) Date of Patent: Nov. 19, 2002

(54) PROCESS FOR THE PREPARATION OF 9-DEOXO-8A-AZA-(8A-ALKYL)-8A-HOMOERYTHROMYCIN A DERIVATIVES FROM 9-DEOXO-9 (Z)-HYDROXYIMINOERYTHROMYCIN A

(75) Inventors: Patrick Leon, Tassin de la Demi Lune (FR); Frederic Lhermitte, Saint Symphorien D'Ozon (FR); Gilles Oddon, Lyons (FR); Denis Pauze, Solaize (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/815,389

(22) Filed: Mar. 22, 2001

(65) Prior Publication Data

US 2001/0047088 A1 Nov. 29, 2001

Related U.S. Application Data

(60) Provisional application No. 60/198,721, filed on Apr. 20, 2000.

(30) Foreign Application Priority Data

Mar. 24, 2000 (FR) .............................................. 00 03807

(51) Int. Cl.[7] .................................................. C07H 1/00
(52) U.S. Cl. ...................................... 536/7.4; 536/18.5
(58) Field of Search ................. 536/7.4, 18.5

(56) References Cited

FOREIGN PATENT DOCUMENTS

| EP | 0 508 726 A1 | 10/1992 |
|---|---|---|
| EP | 0 878 823 A1 | 11/1998 |
| WO | WO 00/58327 | 10/2000 |

Primary Examiner—Elli Peselev
(74) Attorney, Agent, or Firm—Frommer Lawrence & Haug, LLP; William S. Frommer; Thomas J. Kowalski

(57) ABSTRACT

The invention provides a process for the preparation of 9-deoxo-8a-aza-8a-homoerythromycin A

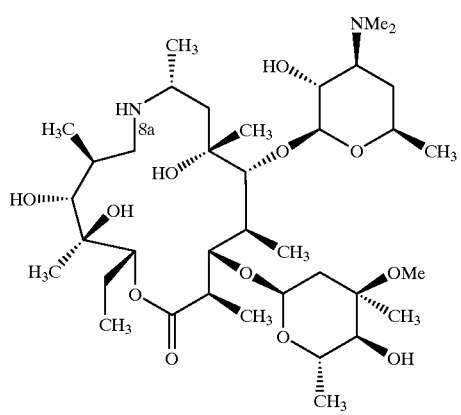

and of its 8a-alkylated derivatives from 9-deoxo-9(Z)-hydroxyiminoerythromycin A via a stereospecific Beckmann rearrangement in a reaction mixture using pyridine as main solvent, resulting in imidate intermediates which are not isolated from said mixture and which are employed directly in a reduction stage using a sufficient amount of borohydride, after extraction of the pyridine with a hydrocarbon which is miscible with the latter and in which said imidates are insoluble. The compound V can be directly N-alkylated at the 8a-position using an aldehyde without being isolated from the reduction mixture.

16 Claims, No Drawings

PROCESS FOR THE PREPARATION OF 9-DEOXO-8A-AZA-(8A-ALKYL)-8A-HOMOERYTHROMYCIN A DERIVATIVES FROM 9-DEOXO-9 (Z)-HYDROXYIMINOERYTHROMYCIN A

RELATED APPLICATIONS

This application claims priority from U.S. application Ser. No. 60/198,721, filed Apr. 20, 2000, and from French application 00 03807, filed Mar. 24, 2000. Each of the foregoing applications, and all documents cited therein or during their prosecution ("appln cited documents") and all documents cited or referenced in the appln cited documents, and all documents cited or referenced herein ("herein cited documents") and all documents cited or referenced in herein cited documents, together with any manufacturer's instructions, descriptions, product specifications, and product sheets for any products mentioned herein, are hereby incorporated herein by reference.

A subject-matter of the present invention is a process for the preparation of 9-deoxo-8a-aza-8a-homoerythromycin A and of its 8a-alkylated derivatives from 9-deoxo-9(Z)-hydroxyiminoerythromycin A.

The present invention relates more particularly to the field of macrolide antibiotics of erythromycin type and more particularly their azamacrolide derivatives, which form the subject-matter of Patent EP 508,699 and correspond to the following general formula:

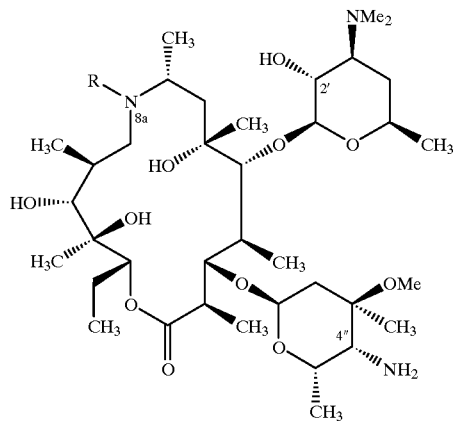

in which R is a hydrogen atom or a $C_1$–$C_{10}$ alkyl, $C_2$–$C_{10}$ alkenyl or $C_6$–$C_{12}$ arylsulfonyl group, if appropriate substituted.

These compounds are obtained from erythromycin A and their synthesis involves two major stages:
- the creation of the 8a-azalide macrocycle from the 9-(E)-oxime of erythromycin A, isomerized to the 9-(Z)-oxime, which is subjected to a stereospecific Beckmann rearrangement, and
- the modification of the cladinose group at the 4"-position, consisting of the conversion of the 4"(S)—OH to 41, "(R)—NH$_2$.

The present invention relates more particularly to the first stage and is aimed at providing a novel process which makes it possible to prepare optionally 8a-alkylated 9-deoxo-8a-aza-8a-homoerythromycin A directly from 9-(Z)-oximeerythromycin A of formula II given hereinbelow.

The conventional synthetic route can be represented diagrammatically in the following way:

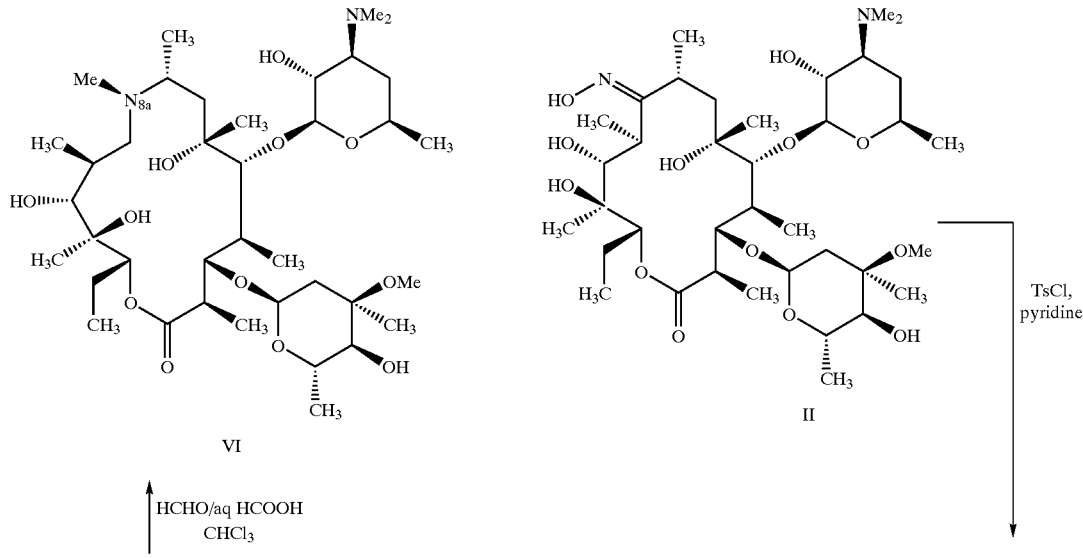

-continued

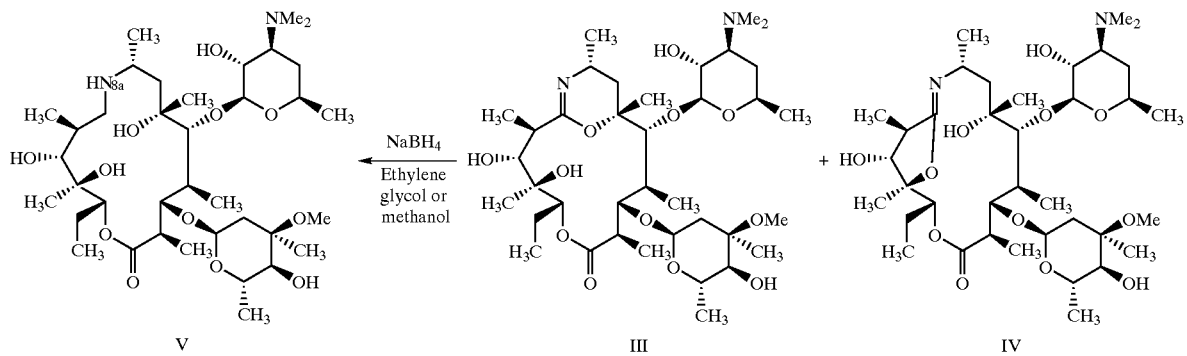

In fact, the current reaction conditions cannot be extrapolated to the industrial scale.

First of all, they require the isolation of the imidate intermediates III and IV. This is because the reduction with sodium borohydride directly on the reaction mixture comprising said imidate intermediates cannot be linked in because of the inhibiting nature of the pyridine. Furthermore, these intermediates are not very stable and readily dehydrate on isolation. This therefore results in a significant drop in the yield.

Furthermore, the imidate of formula IV is sensitive to epimerization at the 10-position, thus resulting in an additional loss of product.

Finally, the reduction conditions currently used, namely sodium borohydride in ethylene glycol or methanol, are not sufficiently effective with regard to the imidate of formula III.

Consequently, it is difficult under current experimental conditions to obtain an overall yield for these two stages, namely Beckmann rearrangement and reduction with sodium borohydride via the intermediate isolation of the two imidates, which is greater than 30%.

A specific object of the present invention is to provide an effective alternative to the synthetic route discussed hereinabove.

More specifically, a subject-matter of the present invention is a process for the preparation of a compound of general formula V via the stereospecific Beckmann rearrangement, in a reaction mixture using pyridine as main solvent, of a compound of general formula II

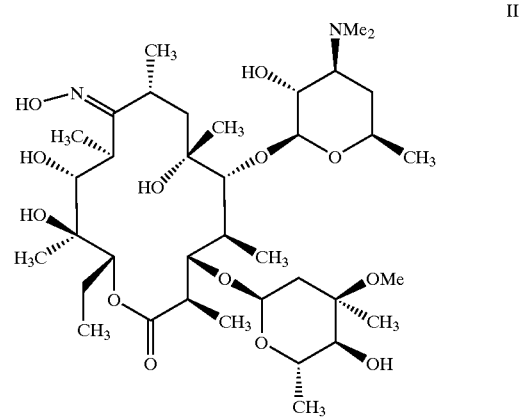

into two intermediate imidates III and IV

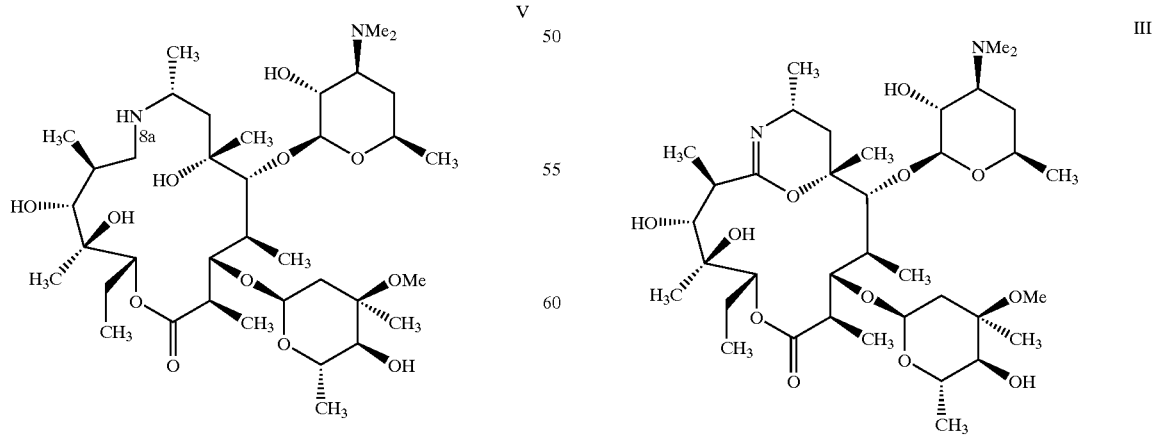

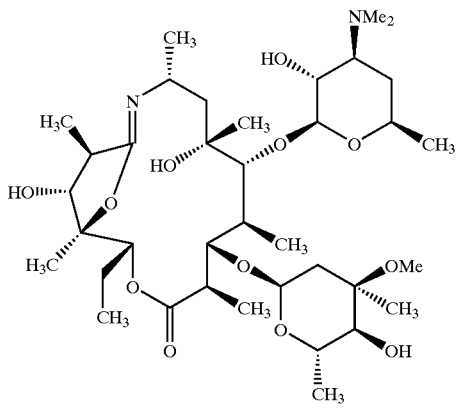

IV and then the reduction of said compounds III and IV, characterized in that said compounds III and IV formed in the reaction mixture of the Beckmann rearrangement are not isolated from said mixture and are employed directly in the reduction stage using a sufficient amount of borohydride, after extraction of the pyridine with a hydrocarbon which is miscible with the latter and in which said imidates III and IV, in the salt form, are insoluble.

According to another characteristic, the process according to the invention is additionally characterized in that the compound of formula V formed on conclusion of the reduction reaction is not isolated from the reaction mixture and is directly N-alkylated therein by the addition of an alkylating reagent to said mixture in an amount sufficient to result in the 9-deoxo-8a-aza-8a-alkyl-8a-homoerythromycin A of formula VI.

The inventors have unexpectedly found that it is possible to reduce the intermediate imidate compounds III and IV with a highly satisfactory yield without isolating them beforehand from said Beckmann rearrangement mixture, with the proviso that the pyridine is extracted from this reaction mixture using a hydrocarbon which is miscible with pyridine and in which the imidates III and IV, protonated at the 3′-dimethylamino group, are insoluble.

It is therefore an opposite approach to the conventional route, which consists in extracting the imidates from the reaction mixture with dichloromethane, after partitioning the residue resulting from the rearrangement comprising them in a water/dichloromethane mixture.

Surprisingly, the use of a hydrocarbon makes it possible to extract and remove the pyridine from the mixture without significant decomposition of the imidate IV and thus makes it possible, on the one hand, to effectively dispense with the stage of isolation of the imidate intermediates, which is harmful in terms of yield and of feasibility on the industrial scale, and, on the other hand, to reduce them more efficiently with an alkali metal borohydride in water and/or an organic solvent. This has the advantage of resulting in an overall yield which is markedly improved with respect to the 30% values mentioned above.

Furthermore, the inventors have also demonstrated that it is possible to N-alkylate the reduced compound obtained directly in the reaction mixture by addition of an aldehyde, without it being necessary to isolate it.

This has the advantages, particularly in the case of N-methylation, of avoiding the use of chloroform and formic acid, such as in the Eschweiler-Clarke process used in particular in the abovementioned Application EP 508 699, and of carrying out the reaction under conditions which are simplified from the viewpoint of temperature and duration.

The process according to the invention will be described in more detail hereinbelow with reference to the following reaction schemes:

Reaction scheme 1

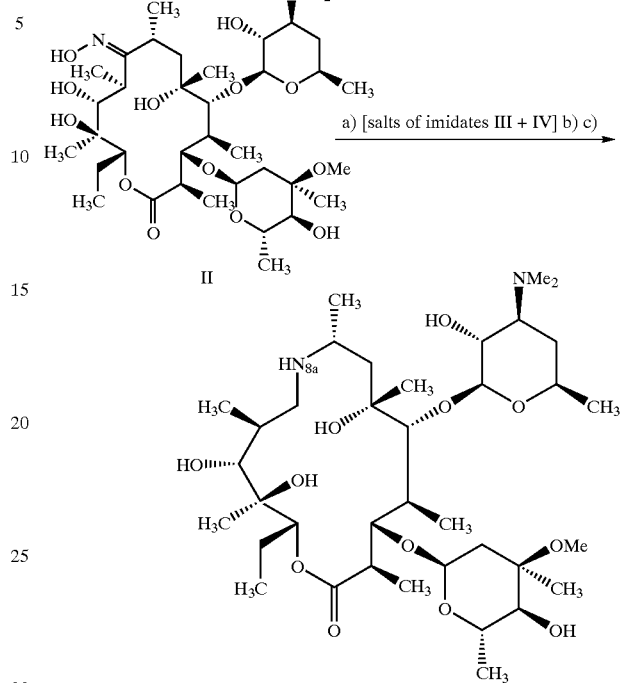

a) TsCL/pyridine
b) hydrocarbon/separation by settling/removal of the organic solvents
c) reduction solvent/NaBH$_4$ Reaction scheme 2

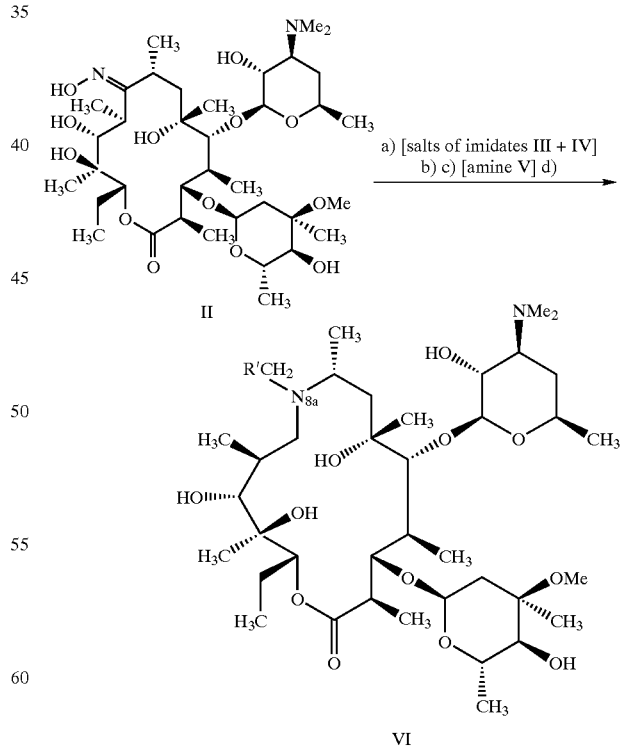

a) TsCL/pyridine
b) hydrocarbon/separation by settling/removal of the organic solvents
c) reduction solvent/NaBH$_4$
d) aq R′CHO With reference to Reaction Scheme 1, the 9-(Z)-oxime of formula II is first of all subjected to a Beckmann rearrangement in a pyridine-based mixture, resulting in the formation of the imidate intermediates III and IV, which are not isolated.

This rearrangement is carried out with sulfonyl chloride preferably selected from tosyl chloride, benzenesulfonyl chloride and mesyl chloride.

According to a preferred embodiment of the invention, the 9-(Z)-oxime of formula II is treated in anhydrous pyridine with tosyl chloride, in the solid form or in solution in an organic solvent, for example in toluene. The amount of tosyl chloride is generally between 1 and 10 equivalents with respect to the 9-(Z)-oxime, preferably between 1.5 and 4 equivalents. The organic solvent is generally present in an amount sufficient to dissolve the tosyl chloride. The reaction is carried out at a temperature preferably of between 0 and 5° C.

After reaction, a hydrocarbon is added to the mixture, which hydrocarbon is miscible with pyridine and the other organic solvents present in said reaction mixture and in which hydrocarbon the imidate intermediates, protonated at the dimethylamino group at the 3'-position, are insoluble. The hydrocarbon is preferably selected from linear-, branched- or cyclic-chain hydrocarbons comprising 5 to 15 carbon atoms. Mention may be made, as representative examples, of pentane, cyclohexane, methylcyclohexane and heptane. It is more preferably heptane.

The mixture is subsequently allowed to separate by settling and the upper phase, comprising the organic solvents, including pyridine, is removed.

The solvent for the reduction reaction, which can be water and/or an organic solvent preferably selected from $C_1$–$C_{10}$ alcohols, preferably methanol or isopropanol, solvents of the amide type, preferably N,N-dimethylformamide or N,N-dimethylacetamide, or solvents of cyclic urea type, preferably 1,3-dimethyl-3,4,5,6-tetrahydro-2(1H)-pyrimidone (DMPU) or 1,3-dimethyl-2-imidazolinone (DMEU), is then added to the residue.

A borohydride, preferably sodium borohydride or potassium borohydride, is subsequently added, the reaction temperature preferably being maintained between 0 and 5° C. The amount of borohydride is generally between 3 and 15 equivalents with respect to the compound to be reduced, preferably between 4 and 5 equivalents.

After reaction, the amine of formula V is either isolated according to Reaction Scheme 1 or directly N-alkylated at the 8a-position according to Reaction Scheme 2.

The amine V can thus be isolated from the reaction mixture according to a conventional procedure which generally involves extraction, washing and then drying operations.

According to another embodiment of the invention, the amine of formula V can be converted directly in the reduction reaction mixture by adding thereto a sufficient amount of an aldehyde of formula R'CHO, with R' being a hydrogen atom or a $C_1$–$C_9$ alkyl or $C_2$–$C_9$ alkenyl group, so as to obtain a compound of general formula VII

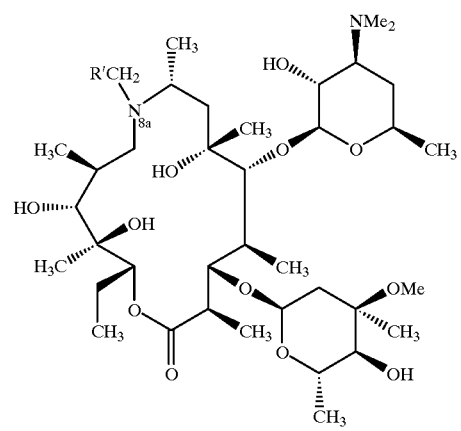

with R' as defined hereinabove.

The aldehyde used is preferably a $C_1$ to $C_4$ aldehyde and more preferably formaldehyde, ethanal or propanal.

In a specific alternative form of this embodiment of the claimed process, formaldehyde is added directly to the reduction reaction mixture comprising the amine V, without isolating it. The reaction temperature is between −10 and +30° C. The reaction duration is generally 2 hours.

The 8a-N-methylated amine of formula VI thus formed

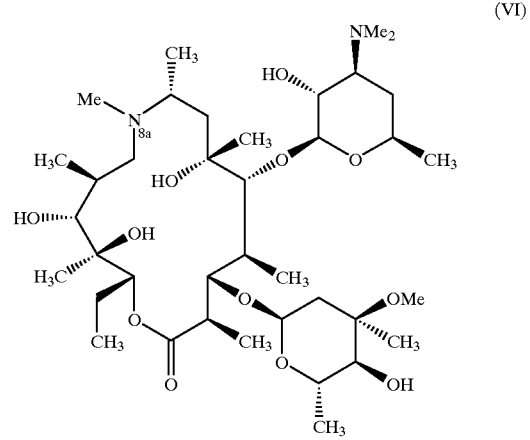

can be isolated according to a conventional procedure which generally involves extraction, washing and then drying operations.

The process according to the invention therefore has the advantage of making it possible to link together the Beckmann rearrangement reaction on 9-(Z)-oximeerythromycin A, carried out in a pyridine-based mixture, and the reaction for the reduction of the imidate intermediates thus formed by a borohydride, without resorting to their isolation.

According to another embodiment, the process according to the invention makes it possible to link in an alkylation reaction, such as a methylation, on the reduced compound, directly in the reduction reaction mixture, under simplified conditions.

The examples which appear hereinbelow are given by way of illustration and without limitation of the present invention.

All the tests are carried out under an inert atmosphere.

EXAMPLE 1

Preparation of 9-deoxo-8a-aza-8a-homoerythromycin A (V) by addition of solid tosyl chloride and reduction in water, according to Reaction Scheme 1:

2 g of (9Z)-9-deoxo-9-hydroxyiminoerythromycin A (2.67 mmol) and then 16 ml of pyridine are introduced into a dry round-bottomed flask rendered inert with argon. The solution is cooled to 0° C. and then 1.32 g of tosyl chloride (6.9 mmol, 2.6 eq.) are introduced portionwise. The reaction mixture is stirred at 0° C. for 1 h 30 and then 20 ml of heptane are added at this temperature. Stirring is halted and the reaction mixture is then allowed to separate by settling. The upper phase is removed by suction, 20 ml of heptane are again added without stirring and then the upper phase is removed by suction.

10 ml of distilled water are added, with stirring and still at 0° C., followed by 0.4 g of sodium borohydride (10.5 mmol, 4 eq.) portionwise. The reaction mixture is allowed to return to room temperature and is stirred for one hour at this temperature. 10 ml of methanol are then added and, after ½ hour, the reaction mixture is acidified to pH=3 using a 2N aqueous hydrochloric acid solution. The aqueous phase is extracted with two times 10 ml of dichloromethane, the organic phases are removed and then the aqueous phase is basified to pH =11 using a 2N aqueous sodium hydroxide solution. After extracting twice with 20 ml of dichloromethane, the organic phases are combined, dried over magnesium sulfate and concentrated under vacuum.

1.73 g of a white solid are obtained, which solid has a purity, quantitatively determined by HPLC, of 69% with regard to 9-deoxo-8a-aza-8a-homoerythromycin A, i.e. a quantitatively determined yield of 60%.

EXAMPLE 2

Preparation of 9-deoxo-8a-aza-8a-homoerythromycin A (V) by addition of a solution of tosyl chloride in toluene and reduction in a water/isopropanol mixture, according to Reaction Scheme 1:

10 g of (9Z)-9-deoxo-9-hydroxyiminoerythromycin A (13.35 mmol) and then 70 ml of pyridine are introduced into a dry round-bottomed flask rendered inert with argon. The solution is cooled to 0° C. and then 6.6 g of tosyl chloride (34.5 mmol, 2.6 eq.), in a solution of 40 ml of toluene, are introduced. The reaction mixture is stirred at 0° C. for 1 h 30 and then 80 ml of heptane are added at this temperature. Stirring is halted and the reaction mixture is then allowed to separate by settling. The upper phase is removed by suction.

70 ml of distilled water and 30 ml of isopropanol are added, with stirring and still at 0° C., followed by 2 g of sodium borohydride (53 mmol, 4 eq.) portionwise. The reaction mixture is allowed to return to room temperature and is stirred for one hour at this temperature. 10 ml of methanol are then added and, after ½ hour, the reaction mixture is acidified to pH=3 using a 2N aqueous hydrochloric acid solution. The aqueous phase is extracted with two times 40 ml of dichloromethane, the organic phases are removed and then the aqueous phase is basified to pH=11 using a 2N aqueous sodium hydroxide solution. After extracting twice with 40 ml of dichloromethane, the organic phases are combined, dried over magnesium sulfate and then concentrated under vacuum.

8.6 g of a white solid are obtained, which solid has a purity, quantitatively determined by HPLC, of 75.5% with regard to 9-deoxo-8a-aza-8a-homoerythromycin A, i.e. a quantitatively determined yield of 65%.

EXAMPLE 3

Preparation of 9-deoxo-8a-aza-8a-homoerythromycin A (V) by addition of tosyl chloride in solution in toluene and reduction in N,N-dimethylformamide, according to Reaction Scheme 1:

20 g of (9Z)-9-deoxo-9-hydroxyiminoerythromycin A (26.7 mmol) and then 160 ml of pyridine are introduced into a dry round-bottomed flask rendered inert with argon. The solution is cooled to 0° C. and then 10.5 g of tosyl chloride (53.4 mmol, 2 eq.), in solution in 60 ml of toluene, are introduced. The reaction mixture is stirred at 0° C. for 1 h 30 and then 260 ml of heptane are added at this temperature. Stirring is halted and the reaction mixture is then allowed to separate by settling. The upper phase is removed by suction.

200 ml of DMF are added, with stirring and still at 0° C., followed by 4 g of sodium borohydride (106 mmol, 4 eq.) portionwise. The reaction mixture is allowed to return to room temperature and is stirred for one hour at this temperature. 20 ml of methanol are then added and, after ½ hour, the reaction mixture is acidified to pH=3 using a 2N aqueous hydrochloric acid solution. The aqueous phase is extracted with two times 50 ml of dichloromethane, the organic phases are removed and then the aqueous phase is basified to pH=11 using a 2N aqueous sodium hydroxide solution. After extracting twice with 100 ml of dichloromethane, the organic phases are combined, dried over magnesium sulfate and then concentrated under vacuum.

18.25 g of a white solid are obtained, which solid has a purity, quantitatively determined by HPLC, of 64.6% with regard to 9-deoxo-8a-aza-8a-homoerythromycin A, i.e. a quantitatively determined yield of 59%.

EXAMPLE 4

Preparation of 9-deoxo-8a-aza-8a-methyl-8a-homoerythromycin A (VI) by addition of tosyl chloride in solution in toluene and reduction in a water/isopropanol mixture, according to Reaction Scheme 2:

20 g of (9z)-9-deoxo-9-hydroxyiminoerythromycin A (26.7 mmol) and then 160 ml of pyridine are introduced into a dry round-bottomed flask rendered inert with argon. The solution is cooled to 0° C. and then 10.5 g of tosyl chloride (53.4 mmol, 2 eq.), in solution of 60 ml of toluene, are introduced. The reaction mixture is stirred at 0° C. for 1 h 30 and then 240 ml of heptane are added at this temperature. Stirring is halted and the reaction mixture is then allowed to separate by settling. The upper phase is removed by suction.

140 ml of water and 60 ml of isopropanol are added, with stirring and still at 0° C., followed by 5 g of sodium borohydride (132.5 mmol, 5 eq.) portionwise. The reaction mixture is allowed to return to room temperature and is stirred for one hour at this temperature.

22.8 g of 35% aqueous formaldehyde (267 mmol, 10 eq.) are subsequently added and the reaction mixture is left for 1 h 30 at room temperature. 20 ml of methanol are then added and, after ½ hour, the reaction mixture is acidified to pH=3 using a 2N aqueous hydrochloric acid solution. The aqueous phase is extracted with two times 50 ml of dichloromethane, the organic phases are removed and then the aqueous phase is basified to pH=11 using a 2N aqueous sodium hydroxide solution. After extracting twice with 100 ml of ethyl acetate, the organic phases are combined, dried over magnesium sulfate and then concentrated under vacuum.

18.4 g of a white solid are obtained, which solid has a purity, quantitatively determined by HPLC, of 69% with regard to 9-deoxo-8a-aza-8a-methyl-8a-homoerythromycin A, i.e. a quantitatively determined yield of 68%.

EXAMPLE 5

Preparation of 9-deoxo-8a-aza-8a-methyl-8a-homoerythromycin A (VI) by addition of a solution of tosyl chloride in toluene and reduction in a water/1,3-dimethyl-2-imidazolinone (DMEU) mixture, according to Reaction Scheme 2:

(9Z)-9-Deoxo-9-hydroxyiminoerythromycin A (150 g, 0.19 mol; purity 94% w/w) and then pyridine (1089 g) are introduced into a dry round-bottomed flask rendered inert with argon. The solution is cooled to −10° C. and then tosyl chloride (76.7 g, 0.4 mol, 2.1 equiv.), in solution in toluene (281 g), is run in over 30 minutes. The reaction mixture is subsequently stirred between −8 and −4° C. for 1 h 30 and then heptane (1011 g) is added at this temperature. Stirring is halted and the reaction mixture is then allowed to separate by settling. The upper phase is removed by suction. The lower viscous phase is diluted a second time with heptane (393 g) without stirring. The upper phase is subsequently removed by suction. The reaction mixture is then diluted with DMEU (140.4 g) and then this solution is added to a solution of sodium borohydride (49.1 g, 1.28 mol, 6.85 equiv.) in water (1227 g). After returning to room temperature, the reaction mixture is stirred for 2 hours at this temperature. The mixture is subsequently treated with methanol (351.1 g) and then with 37% aqueous formaldehyde (140 g, 1.73 mol, 9.2 equiv.). The mixture is maintained at room temperature for 2 h. The reaction mixture is subsequently acidified to pH=4 using a 36% aqueous hydrochloric acid solution. The aqueous phase is extracted with toluene (355 g). The aqueous phase is subsequently basified to pH=10 using a 30% w/w aqueous sodium hydroxide solution. After extracting twice with toluene (2×355 g) at 50° C., the organic phases are combined, washed at 50° C. with water (322 g) and concentrated under vacuum. The organic phase thus obtained is taken up several times in heptane in order to distil off the heptane/pyridine azeotrope under vacuum.

151 g of a white solid are obtained, which solid has a purity, quantitatively determined by HPLC, of 65% with regard to 9-deoxo-8a-aza-8a-methyl-8a-homoerythromycin A, i.e. a quantitatively determined yield of 60%.

The invention shall now be further described by way of the following numbered paragraphs:

1. Process for the preparation of 9-deoxo-8a-aza-8a-homoerythromycin A of formula V

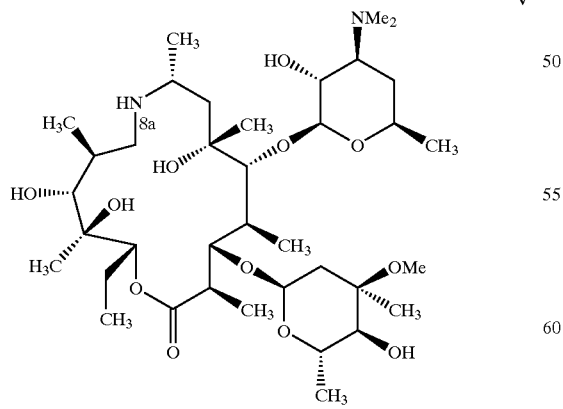

via the stereospecific Beckmann rearrangement, in a reaction mixture using pyridine as main solvent, of a compound of formula II

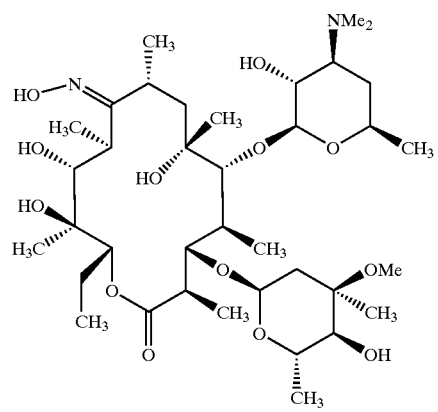

into two imidate intermediates III and IV

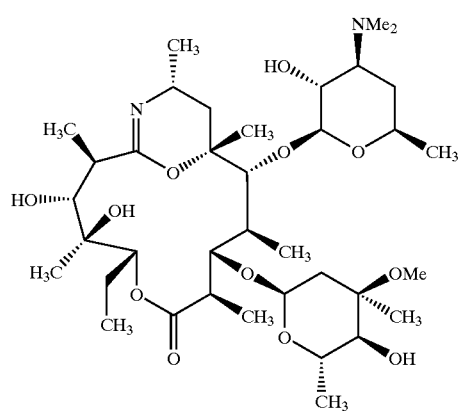

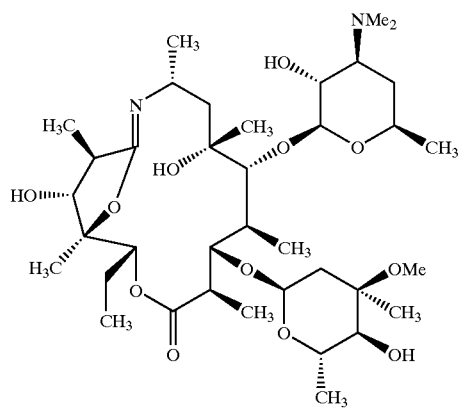

and then the reduction of said compounds III and IV, characterized in that said compounds III and IV formed in the reaction mixture of the Beckmann rearrangement are not isolated from said mixture and are employed directly in the reduction stage using a sufficient amount of a borohydride, after extraction of the pyridine with a hydrocarbon which is miscible with the latter and in which said imidates III and IV, in the salt form, are insoluble.

2. Process according to Paragraph 1, characterized in that the Beckmann rearrangement is carried out using sulfonyl chloride, preferably selected from tosyl chloride, benzenesulfonyl chloride and mesyl chloride.

3. Process according to Paragraph 1 or 2, characterized in that the hydrocarbon is selected from linear-, branched- or cyclic-chain hydrocarbons comprising 5 to 15 carbon atoms, in particular from pentane, cyclohexane, methyl-cyclohexane and heptane, and is preferably heptane.

4. Process according to any one of the preceding paragraphs, characterized in that the organic solvents present in the mixture for the Beckmann rearrangement, comprising pyridine, are removed by separation by settling.

5. Process according to any one of Paragraphs 1 to 4, characterized in that, after removing the organic solvents, including pyridine, from the Beckmann rearrangement mixture, the solvent for the reduction reaction, which is water, is added to the residue.

6. Process according to any one of Paragraphs 1 to 4, characterized in that, after removing the organic solvents, including pyridine, from the Beckmann rearrangement mixture, the solvent for the reduction reaction, which is an organic solvent selected from $C_1$–$C_{10}$ alcohols, preferably methanol or isopropanol, or which is a mixture of a preceding solvent and water, is added to the residue.

7. Process according to any one of Paragraphs 1 to 4, characterized in that, after removing the organic solvents, including pyridine, from the Beckmann rearrangement mixture, the solvent for the reduction reaction, which is of amide type and which is preferably N,N-dimethylformamide or N,N-dimethylacetamide, or which is a mixture of a preceding solvent and water, is added to the residue.

8. Process according to any one of Paragraphs 1 to 4, characterized in that, after removing the organic solvents, including pyridine, from the Beckmann rearrangement mixture, the solvent for the reduction reaction, which is of cyclic urea type, preferably 1,3-dimethyl-3,4,5,6-tetrahydro-2(1H)-pyrimidone (DMPU) or 1,3-dimethyl-2-imidazolinone (DMEU), or which is a mixture of a preceding solvent and water, is added to the residue.

9. Process according to any one of the preceding paragraphs, characterized in that the reduction reaction is carried out with sodium borohydride or potassium borohydride.

10. Process according to any one of the preceding paragraphs, characterized in that the compound of formula V formed on conclusion of the reduction reaction is not isolated from the reaction mixture and is directly converted therein by addition of a sufficient amount of an aldehyde R'CHO to result in a compound of formula VII

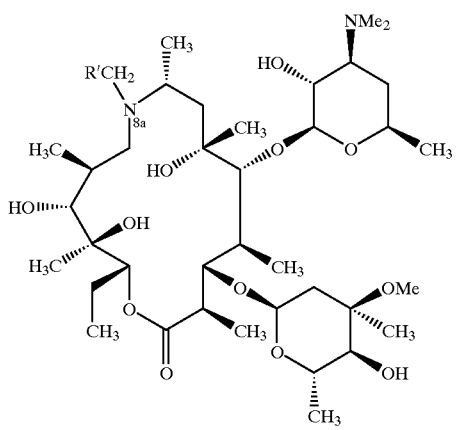

in which R' is a hydrogen atom or a $C_1$–$C_9$ alkyl or $C_2$–$C_9$ alkenyl group.

11. Process according to Paragraph 10, characterized in that the aldehyde used is a $C_1$ to $C_4$ aldehyde.

12. Process according to Paragraph 10 or 11, characterized in that formaldehyde is used as aldehyde to result in 9-deoxo-8a-aza-8a-methyl-8a-homoerythromycin A of following formula VI:

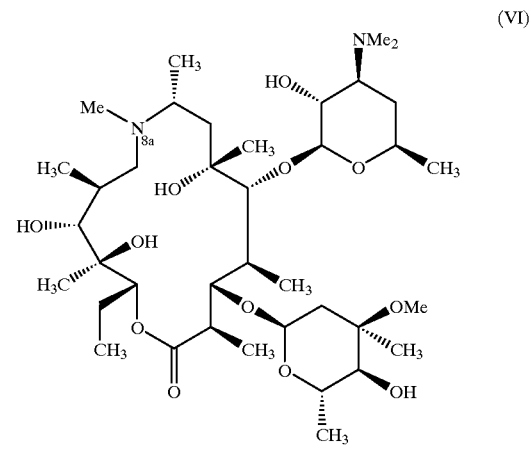

What is claimed is:

1. Process for the preparation of 9-deoxo-8a-aza-8a-homoerythromycin A of formula V

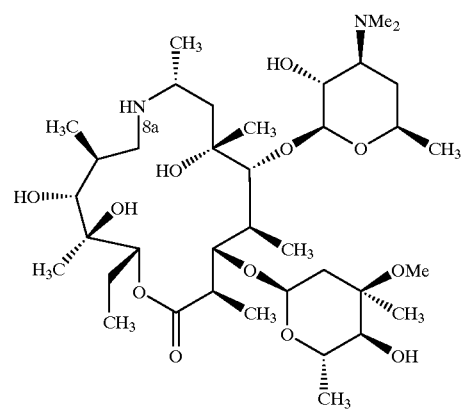

via the stereospecific Beckmann rearrangement, in a reaction mixture using pyridine as main solvent, of a compound of formula II

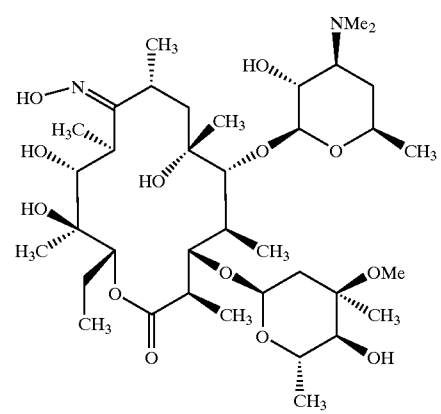

into two imidate intermediates III and IV

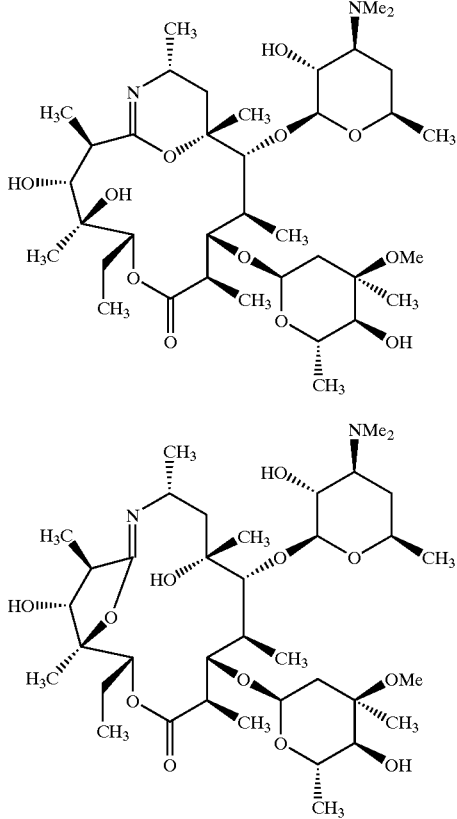

and then the reduction of said compounds III and IV, characterized in that said compounds III and IV formed in the reaction mixture of the Beckmann rearrangement are not isolated from said mixture and are employed directly in the reduction stage using a sufficient amount of a borohydride, after extraction of the pyridine with a hydrocarbon which is miscible with the latter and in which said imidates III and IV, in the salt form, are insoluble.

2. The process according to claim 1, wherein the Beckmann rearrangement is carried out using sulfonyl chloride, selected from the group consisting of tosyl chloride, benzenesulfonyl chloride and mesyl chloride.

3. The process according to claim 1, wherein the hydrocarbon is selected from the group consisting of linear-, branched- or cyclic-chain hydrocarbons with 5 to 15 carbon atoms.

4. The process according to claim 1, wherein the organic solvents present in the mixture for the Beckmann rearrangement, are removed by separation by settling.

5. The process according to claim 1, wherein after removing the organic solvents from the Beckmann rearrangement mixture, the solvent for the reduction reaction, which is water, is added to the residue.

6. The process according to claim 1, wherein after removing the organic solvents from the Beckmann rearrangement mixture, the solvent for the reduction reaction, which is an organic solvent selected from the group consisting of $C_1$–$C_{10}$ alcohols, or which is a mixture of a preceding solvent and water, is added to the residue.

7. The process according to claim 1, wherein after removing the organic solvents from the Beckmann rearrangement mixture, the solvent for the reduction reaction, which is of amide type, or which is a mixture of a preceding solvent and water, is added to the residue.

8. The process according to claim 1, wherein after removing the organic solvents from the Beckmann rearrangement mixture, the solvent for the reduction reaction, which is of cyclic urea type, or which is a mixture of a preceding solvent and water, is added to the residue.

9. The process according to claim 1, wherein the reduction reaction is carried out with sodium borohydride or potassium borohydride.

10. The process according to claim 1, wherein the compound of formula V formed on conclusion of the reduction reaction is not isolated from the reaction mixture and is directly converted therein by addition of a sufficient amount of an aldehyde R'CHO to result in a pound of formula VII

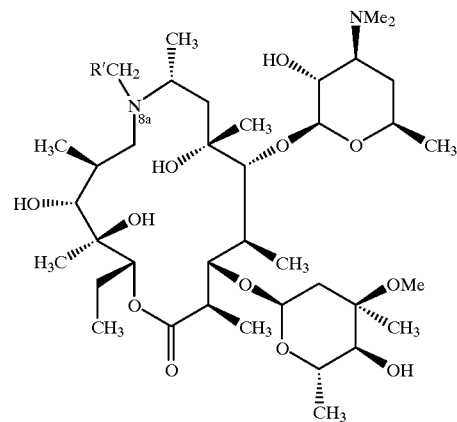

in which R' is a hydrogen atom or a $C_1$–$C_9$ alkyl or $C_2$–$C_9$ alkenyl group.

11. The process according to claim 10, wherein the aldehyde used is a C1 to C4 aldehyde.

12. The process according to claim 10, wherein formaldehyde is used as aldehyde to result in 9-deoxo-8a-aza-8a-methyl-8a-homoerythromycin A of following formula VI:

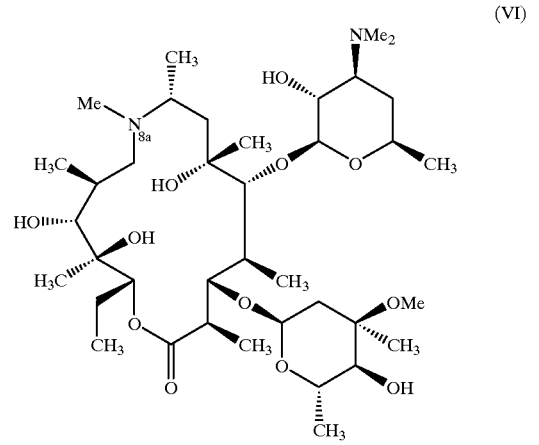

13. The process according to claim 3, wherein the hydrocarbon is selected from the group consisting of pentane, cyclohexane, methylcyclohexane and heptane.

14. The process according to claim 6, wherein the organic solvent is selected from the group consisting of methanol and isopropanol.

15. The process according to claim 7, wherein the solvent for the reduction reaction is selected from the group consisting of N,N dimethylformamide and N,N-dimethylacetamide.

16. The process according to claim 8, wherein the solvent for the reduction reaction is selected from the group consisting of 1,3-dimethyl-3,4,5,6-tetrahydro-2(1H)-pyrimidone (DMPU) and 1,3-dimethyl-2-imidazolinone (DMEU).

* * * * *

UNITED STATES PATENT AND TRADEMARK OFFICE
CERTIFICATE OF CORRECTION

PATENT NO. : 6,482,931 B2  
DATED : November 19, 2002  
INVENTOR(S) : Patrick Leon et al.

Page 1 of 1

It is certified that error appears in the above-identified patent and that said Letters Patent is hereby corrected as shown below:

<u>Title page,</u>
Item [75], Inventors, change "Lyons" to -- Lyon --.
Item [73], Assignee, change "Lyons" to -- Lyon --.

Signed and Sealed this

Fourth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,482,931 B2
DATED         : November 19, 2002
INVENTOR(S)   : Patrick Leon et al.

Page 1 of 1

It is certified that error appears in the above-identified patent and that said Letters Patent is hereby corrected as shown below:

<u>Column 16,</u>
Line 14, change "to result in a pound of formula VII" to -- result in a compound of formula VII --.
Line 37, change "aldehyde used is a C1 to C4 aldehyde" to -- aldehyde used is a $C_1$ to $C_4$ aldehyde --.

Signed and Sealed this

Thirtieth Day of December, 2003

JAMES E. ROGAN
*Director of the United States Patent and Trademark Office*